United States Patent [19]
Schäfer et al.

[11] Patent Number: 5,733,850
[45] Date of Patent: Mar. 31, 1998

[54] SUBSTITUTED 2-PHENYLPYRIDINES

[75] Inventors: Peter Schäfer, Ottersheim; Gerhard Hamprecht, Weinheim; Elisabeth Heistracher, Ludwigshafen; Ralf Klintz, Gruenstadt; Hartmann König, Heidelberg; Albrecht Harreus, Ludwigshafen; Norbert Götz, Worms; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[21] Appl. No.: 860,022

[22] PCT Filed: Jan. 4, 1996

[86] PCT No.: PCT/EP96/00007

§ 371 Date: Jul. 3, 1997

§ 102(e) Date: Jul. 3, 1997

[87] PCT Pub. No.: WO96/21645

PCT Pub. Date: Jul. 18, 1996

[30] Foreign Application Priority Data

Jan. 13, 1995 [DE] Germany .......... 19 500 758.1

[51] Int. Cl.⁶ .......... A01N 43/40; C07D 213/89
[52] U.S. Cl. .......... 504/244; 504/254; 504/255; 504/251; 504/260; 546/284.4; 546/286; 546/291; 546/304; 546/314; 546/316; 546/339; 546/341; 546/342
[58] Field of Search .......... 546/284.4, 286, 546/291, 304, 314, 316, 318, 339, 341, 342; 504/254, 255, 260, 244, 251

[56] References Cited

U.S. PATENT DOCUMENTS

| 3,449,349 | 6/1969 | Shen et al. | 546/284.4 |
| 3,697,251 | 10/1972 | Long et al. | 546/316 |
| 4,394,155 | 7/1983 | Plant et al. | 546/294 |
| 4,793,466 | 12/1988 | Katoh et al. | 514/256 |
| 4,826,531 | 5/1989 | Anthony et al. | 504/244 |
| 5,284,956 | 2/1994 | Buchecker et al. | 546/339 |
| 5,292,757 | 3/1994 | Ohsumi et al. | 514/332 |
| 5,310,919 | 5/1994 | Klausener et al. | 546/301 |
| 5,405,828 | 4/1995 | Banji et al. | 504/246 |
| 5,438,033 | 8/1995 | Drumm et al. | 504/130 |

FOREIGN PATENT DOCUMENTS

| 0463492 | 1/1992 | European Pat. Off. . |
| 0548593 | 6/1993 | European Pat. Off. . |
| 05533630 | 8/1993 | European Pat. Off. . |
| 4335810 | 4/1994 | Germany . |
| 4323916 | 1/1995 | Germany . |

OTHER PUBLICATIONS

Chem. Abs., vol. 114, No. 11, Mel'Ni Kova et al. (Mar. 18, 1991).

Chem. Abs., vol. 125, No. 195679, Kleemann et al. (1996).

*Primary Examiner*—Deborah Lambkin
*Attorney, Agent, or Firm*—Keil & Weinkauf

[57] ABSTRACT

Substituted 2-phenylpyridines I

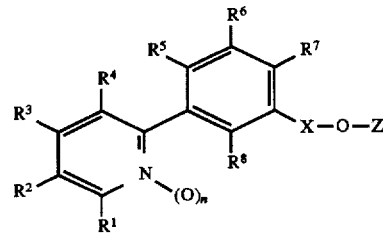

where the substituents have the meaning given in the specification and their use.

16 Claims, No Drawings

SUBSTITUTED 2-PHENYLPYRIDINES

This application is a 371 of PCT/EP96/00007 filed Jan. 4, 1996.

The present invention relates to novel substituted 2-phenylpyridines of the formula I where the variables have the following meanings:

n is 0 or 1;

$R^1$, $R^3$ and $R^4$ independently of one another are hydrogen, halogen, $C_1$–$C_4$-alkyl, $C_1$–$C_4$-haloalkyl, hydroxyl, $C_1$–$C_4$-alkoxy, $C_1$–$C_4$-haloalkoxy, nitro, amino, $C_1$–$C_4$-alkylamino, di-($C_1$–$C_4$-alkyl)-amino, mercapto, $C_1$–$C_4$-alkylthio, $C_1$–$C_4$-haloalkylthio, cyano, carboxyl, ($C_1$–$C_4$-alkoxy)carbonyl, aminocarbonyl, $C_1$–$C_4$-alkylaminocarbonyl or di-($C_1$–$C_4$-alkyl)-aminocarbonyl;

$R^2$ is hydrogen, halogen, $C_1$–$C_4$-alkyl, $C_1$–$C_4$-haloalkyl, cyano, nitro, amino, hydroxyl, $C_1$–$C_4$-alkoxy, $C_1$–$C_4$-haloalkoxy, mercapto, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^5$ is hydrogen, halogen or cyano;

$R^6$ and $R^8$ independently of one another are hydrogen or halogen;

$R^7$ is hydrogen, cyano, nitro, hydroxyl, trifluoromethylsulfonyloxy, halogen, $C_1$–$C_4$-alkyl, $C_1$–$C_4$-haloalkyl, $C_1$–$C_4$-alkoxy or $C_1$–$C_4$-haloalkoxy;

X is one of the following bridges:

—CO—, —O—C($R^9$, $R^{10}$)—CO—, —S—C($R^9$, $R^{10}$)—CO—, —CH$_2$—CH($R^{11}$)—CO— or —CH=C($R^{11}$)—CO—, where $R^9$ and $R^{10}$ independently of one another are hydrogen or $C_1$–$C_4$-alkyl and $R^{11}$ is hydrogen, halogen or $C_1$–$C_4$-alkyl;

Z is a group $R^{12}$ is hydrogen, hydroxyl, halogen, $C_1$–$C_4$-alkyl, $C_1$–$C_4$-alkoxy, ($C_1$–$C_4$-alkyl)carbonyloxy, ($C_1$–$C_4$-haloalkyl)carbonyloxy, ($C_3$–$C_6$-cycloalkyl)carbonyloxy, benzoyloxy, benzylcarbonyloxy, benzyloxy, ($C_1$–$C_4$-alkoxy)carbonyloxy, ($C_1$–$C_4$-alkyl-amino)carbonyloxy, di-($C_1$–$C_4$-alkyl)-aminocarbonyloxy or $C_1$–$C_3$-alkylsulfonyloxy;

$R^{13}$ and $R^{14}$ independently of one another are hydrogen, hydroxyl, $C_1$–$C_4$-alkyl, $C_1$–$C_4$-alkoxy or ($C_1$–$C_4$-alkyl)carbonyloxy;

$R^{15}$ is hydrogen or $C_1$–$C_4$-alkyl and $R^{16}$ and $R^{17}$ independently of one another are hydroxyl, $C_1$–$C_6$-alkoxy, $C_3$–$C_6$-alkenyloxy, $C_3$–$C_6$-alkynyloxy, $C_1$–$C_6$-alkoxy-$C_2$–$C_4$-alkoxy, $C_3$–$C_6$-cycloalkyloxy, amino, $C_1$–$C_4$-alkylamino, di-($C_1$–$C_4$-alkyl)-amino, N-pyrrolidinyl, N-piperidinyl, N-morpholinyl, $C_3$–$C_6$-cycloalkylamino, di-($C_3$–$C_6$-cycloalkyl)-amino, $C_3$–$C_6$-alkenylamino or $C_3$–$C_6$-alkynylamino or $R^{16}$ and $R^{17}$ together are a bridge —N($R^{18}$)—N($R^{19}$)— or —N($R^{20}$)—, where $R^{18}$ and $R^{19}$ are in each case hydrogen or $C_1$–$C_4$-alkyl and $R^{20}$ is hydrogen, $C_1$–$C_6$-alkyl, $C_3$–$C_6$-alkenyl, $C_3$–$C_6$-alkynyl, $C_1$–$C_6$-alkoxy or $C_3$–$C_6$-alkenyloxy, or the agriculturally utilizable salts of the compounds I, if these exist.

The invention additionally relates to the use of the compounds I as herbicides and/or for the desiccation and/or defoliation of plants, herbicidal compositions and compositions for the desiccation and/or defoliation of plants, which contain the compounds I as active substances, processes for the control of undesired vegetation and for the desiccation and/or defoliation of plants using the compounds I, processes for preparing the compounds I and herbicidal compositions and compositions for the desiccation and/ or defoliation of plants using the compounds I, and also intermediates of the formula III and a process for their preparation.

In the earlier German Application DE-A 43 23 916, inter alia, 2-phenylpyridines of the compound I type are described as herbicides and as compounds having desiccant/defoliant activity. Suitable choice of the substituents results, inter alia, in compounds of the formula IIa where $R^{2'}$ is halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{4'}$ is hydrogen, nitro, amino, cyano, hydroxyl, mercapto, hydroxycarbonyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-($C_1$–$C_4$-alkyl)-amino, $C_1$–$C_4$-alkylthio, $C_1$–$C_4$-haloalkylthio or ($C_1$–$C_4$-alkoxy)carbonyl;

$R^{5'}$ is hydrogen or halogen;

$R^{7'}$ is cyano, nitro, hydroxyl, halogen or trifluoromethyl;

$R^a$ is alkoxycarbonylalkoxy or various organic radicals which can be bonded, inter alia, via —CO—, —CH$_2$—CH(halogen)—CO— or —C=C($R^{11}$)—CO—.

EP-A 548 593 additionally discloses that compounds of the formula IIb where Het is various heterocycles and Y, inter alia, is a bond, —OCH$_2$—, —OCH($C_{1-4}$-alkyl)—, —SCH$_2$— or —S—CH ($C_{1-4}$-alkyl) and $R^b$ is H, OH, halogen, $C_{1-4}$-alkoxy, benzyloxy, $C_{1-3}$-alkylsulfonyloxy or certain radicals —O—CO—R, are herbicidally active.

In addition, DE-A 43 35 810 discloses that 3-phenyluracil derivatives in which the phenyl ring carries a group —CO—O—C($R^{15}$, $COR^c$)—$CH_2$—$COR^d$ in the meta-position to the uracil moiety, where $COR^c$ and $COR^d$ are ester, thioester or acid amide radicals or $R^c$ and $R^d$ together form a nitrogen or dinitrogen bridge, are also herbicidally active.

The herbicidal action of the known compounds with respect to the weeds, however, is not always completely satisfactory.

It is therefore an object of the present invention to provide novel herbicidally active compounds using which undesired plants can be specifically controlled better than previously. The object also extends to the provision of novel compounds having desiccant/defoliant activity.

We have found that this object is achieved by the substituted 2-phenylpyridines of the formula I having herbicidal action which are defined at the outset and novel intermediates III for their preparation.

Herbicidal compositions were further found which comprise the compounds I and have a very good herbicidal action. Processes for the preparation of these compositions and processes for controlling undesired vegetation using the compounds I were additionally found.

In addition, it was found that the compounds I are also suitable for the defoliation and desiccation of parts of plants, for which crop plants such as cotton, potato, oilseed, rape, sunflower, soybean or field beans, in particular cotton, are suitable. With respect to this, compositions for the desiccation and/or defoliation of plants, processes for preparing these compositions and processes for the desiccation and/or defoliation of plants using the compounds I were found.

Depending on the substitution pattern, the compounds of the formula I can contain one or more centers of chirality and then exist as enantiomer or diastereomer mixtures. The invention relates both to the pure enantiomers or diastereomers and to their mixtures.

The substituted 2-phenylpyridines I can be present in the form of their agriculturally utilizable salts, where the nature of the salt generally does not matter. In general, the salts of those bases and those acid addition salts are suitable in which the herbicidal action is not adversely affected in comparison with the free compound I.

Suitable salts are particularly those of the alkali metals, preferably sodium and potassium salts, the alkaline earth metals, preferably calcium and magnesium salts, those of the transition metals, preferably zinc and iron salts, and also ammonium salts in which the ammonium ion, if desired, can carry one to four $C_1-C_4$-alkyl or hydroxy-$C_1-C_4$-alkyl substituents and/or a phenyl or benzyl substituent, preferably diisopropylammonium, tetramethylammonium, tetrabutylammonium, trimethylbenzylammonium and trimethyl(2-hydroxyethyl)ammonium salts, in addition phosphonium salts or sulfonium salts such as, preferably, tri($C_1-C_4$-alkyl)sulfonium salts, and sulfoxonium salts such as, preferably, tri($C_1-C_4$-alkyl)sulfoxonium salts.

The acid addition salts which may be mentioned are primarily the hydrochlorides and hydrobromides, sulfates, nitrates, phosphates, oxalates and the dodecylbenzenesulfonates.

The names alkyl, haloalkyl, alkoxy, haloalkoxy, alkoxyalkoxy, alkylthio, haloalkylthio, alkylamino, dialkylamino, cycloalkyloxy, cycloalkylamino, dicycloalkylamino, alkoxycarbonyl, alkoxycarbonyloxy, alkylcarbonyloxy, haloalkylcarbonyloxy, cycloalkylcarbonyloxy, alkylaminocarbonyl, dialkylaminocarbonyl, alkylaminocarbonyloxy, dialkylaminocarbonyloxy, alkylsulfinyl, haloalkylsulfinyl, alkylsulfonyl, haloalkylsulfonyl, alkylsulfonyloxy, alkenyl, alkynyl, alkenyloxy, alkynyloxy, alkenylamino and alkynylamino used in the definition of the substituents $R^1$ to $R^{20}$ are, like the meaning halogen, collective terms for individual lists of the separate group members. All carbon chains, ie. all alkyl, haloalkyl, alkenyl and alkynyl moieties, can be straight-chain or branched. Halogenated substituents preferably carry one to five identical or different halogen atoms.

Specific examples are:

halogen: fluorine, chlorine, bromine or iodine;

$C_1-C_4$-alkyl and the alkyl moiety of ($C_1-C_4$-alkyl) carbonyloxy: methyl, ethyl, n-propyl, 1-methylethyl, n-butyl, 1-methylpropyl, 2-methylpropyl or 1,1-dimethylethyl;

$C_1-C_4$-haloalkyl and the haloalkyl moiety of ($C_1-C_4$-haloalkyl)-carbonyloxy: a $C_1-C_4$-alkyl radical such as mentioned above, which is partially or completely substituted by fluorine, chlorine, bromine and/or iodine, ie., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluorethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1-C_4$-alkoxy and the alkoxy moiety of ($C_1-C_4$-alkoxy) carbonyloxy: methoxy, ethoxy, n-propoxy, 1-methylethoxy, n-butoxy, 1-methylpropoxy, 2-methylpropoxy or 1,1-dimethylethoxy;

$C_1-C_6$-alkoxy: $C_1-C_4$-alkoxy as mentioned above, and also n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1-C_4$-haloalkoxy: $C_1-C_4$-alkoxy as mentioned above, which is partially or completely substituted by fluorine, chlorine, bromine and/or iodine, ie., for example, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-alkoxy-$C_2$–$C_4$-alkoxy: $C_2$–$C_6$-alkoxy substituted by $C_1$–$C_6$-alkoxy as mentioned above, ie., for example, 2-(methoxy)ethoxy, 2-(ethoxy)ethoxy, 2-(n-propoxy) ethoxy, 2-(1-methylethoxy)ethoxy, 2-(n-butoxy) ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(n-propoxy)propoxy, 2-(1-methylethoxy)propoxy, 2-(n-butoxy)propoxy, 2-(1-methylpropoxy)propoxy, 2-(2-methylpropoxy)propoxy, 2-(1,1-dimethylethoxy) propoxy, 2-(n-pentoxy)propoxy, 2-(n-hexoxy)propoxy, 3-(methoxy)propoxy, 3-(ethoxy)propoxy, 3-(n-propoxy)propoxy, 3-(1-methylethoxy)propoxy, 3-(n-butoxy)propoxy, 3-(1-methylpropoxy)propoxy, 3-(2-methylpropoxy)propoxy, 3-(1,1-dimethylethoxy) propoxy, 3-(n-pentoxy)propoxy, 3-(n-hexoxy)propoxy, 2-(methoxy)butoxy, 2-(ethoxy)butoxy, 2-(n-propoxy) butoxy, 2-(1-methylethoxy)butoxy, 2-(n-butoxy) butoxy, 2-(1-methylpropoxy)butoxy, 2-(2-methylpropoxy)butoxy, 2-(1,1-dimethylethoxy)butoxy, 2-(n-pentoxy)butoxy, 2-(n-hexoxy)butoxy, 3-(methoxy)butoxy, 3-(ethoxy)butoxy, 3-(n-propoxy) butoxy, 3-(1-methylethoxy)butoxy, 3-(n-butoxy) butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy) butoxy, 4-(1-methylethoxy)butoxy, 4-(n-butoxy) butoxy, 4-(1-methylpropoxy)butoxy, 4-(2-methylpropoxy)butoxy, 4-(1,1-dimethylethoxy)butoxy, 2-(n-pentoxy)butoxy or 2-(n-hexoxy)butoxy;

$C_1$–$C_4$-alkylthio: methylthio, ethylthio, n-propylthio, 1-methylethylthio, n-butylthio, 1-methylpropylthio, 2-methylpropylthio or 1,1-dimethylethylthio;

$C_1$–$C_4$-haloalkylthio: $C_1$–$C_4$-alkylthio as mentioned above, which is partially or completely substituted by fluorine, chlorine, bromine and/or iodine, ie., for example, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluorethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_4$-alkylamino and the alkylamino moieties of ($C_1$–$C_4$-alkylamino)carbonyl and $C_1$–$C_4$-alkylaminocarbonyloxy: methylamino, ethylamino, n-propylamino, 1-methylethylamino, n-butylamino, 1-methylpropylamino, 2-methylpropylamino or 1,1-dimethylethylamino;

di-($C_1$–$C_4$-alkyl)amino and the dialkylamino moieties of di-($C_1$–$C_4$-alkyl)aminocarbonyl and di-($C_1$–$C_4$-alkyl) aminocarbonyloxy: eg. N,N-dimethylamino, N,N-diethylamino, N,N-diisopropylamino, N,N-dibutylamino, N,N-di-(1-methylpropyl)amino, N,N-di-(2-methylpropyl)amino, N,N-di-(1,1-dimethylethyl) amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl) amino, N-(1,1-dimethylethyl)-N-methylamino, N-ethyl-N-propylamino, N-ethyl-N-(1-methylethyl) amino, N-butyl-N-ethylamino, N-ethyl-N-(1-methylpropyl)amino, N-ethyl-N-(2-methylpropyl) amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethyl-ethyl)-N-(2-methylpropyl)amino;

$C_1$–$C_4$-alkylsulfinyl: methylsulfinyl, ethylsulfinyl, n-propylsulfinyl, 1-methylethylsulfinyl, n-butylsulfinyl, 1-methylpropylsulfinyl, 2-methylpropylsulfinyl or 1,1-dimethylethylsulfinyl;

$C_1$–$C_4$-haloalkylsulfinyl: $C_1$–$C_4$-alkylsulfinyl as mentioned above, which is partially or completely substituted by fluorine, chlorine, bromine and/or iodine, ie., for example, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluorpropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl or nonafluorobutylsulfinyl;

$C_1$–$C_4$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl or 1,1-dimethylethylsulfonyl;

$C_1$–$C_4$-haloalkylsulfonyl: $C_1$–$C_4$-alkylsulfonyl as mentioned above, which is partially or completely substituted by fluorine, chlorine, bromine and/or iodine, ie., for example, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2- trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl;

$C_1$–$C_3$-alkylsulfonyloxy: methylsulfonyloxy, ethylsulfonyloxy, n-propylsulfonyloxy or 1-methylethylsulfonyloxy;

the cycloalkyl moieties of ($C_3$–$C_6$-cycloalkylcarbonyloxy, $C_3$–$C_6$-cycloalkylamino and di-($C_3$–$C_6$-cycloalkyl)amino: cyclopropyl, cyclobutyl, cyclopentyl or cyclohexyl;

$C_3$–$C_6$-alkenyl and the alkenyl moieties of $C_3$–$C_6$-alkenyloxy and $C_3$–$C_6$-alkenylamino: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_3$–$C_6$-alkynyl and the alkynyl moieties of $C_3$–$C_6$-alkynyloxy and $C_3$–$C_6$-alkynylamino: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl.

With respect to the use of the compounds of the formula I according to the invention as herbicides and/or as active compounds having defoliant/desiccant activity, the variables preferably have the following meanings, namely in each case per se or in combination:

n is zero;

$R^1$, $R^3$, $R^4$ and $R^5$ independently of one another are hydrogen or halogen;

$R^2$ is halogen or $C_1$–$C_4$-haloalkyl having one to five halogen atoms;

$R^6$ and $R^8$ are hydrogen;

$R^7$ is cyano or halogen;

$R^9$ and $R^{10}$ independently of one another are hydrogen or $C_1$–$C_4$-alkyl;

$R^{11}$ is hydrogen or halogen;

$R^{12}$, $R^{13}$ and $R^{14}$ independently of one another are hydrogen, hydroxyl, $C_1$–$C_4$-alkyl or ($C_1$–$C_4$-alkyl) carbonyloxy;

$R^{15}$ is hydrogen;

$R^{16}$ and $R^{17}$ independently of one another are $C_1$–$C_6$-alkoxy, $C_3$–$C_6$-alkenyloxy, amino, $C_1$–$C_4$-alkylamino, di-($C_1$–$C_4$-alkyl)amino or together a bridge —NH—NH—, —N($C_1$–$C_4$-alkyl)—N($C_1$–$C_4$-alkyl)— or —N($R^{20}$)—, where $R^{20}$ is hydrogen or $C_1$–$C_4$-alkyl.

Particularly preferred compounds are the compounds Ia (=I where n=zero; $R^1$, $R^3$, $R^6$ and $R^8$=hydrogen) listed in Table 1 below:

TABLE 1

H$_3$C–CO–O structure; Ia

M.p. [°C.];
IR data
($\gamma$[cm$^{-1}$]);
$^1$H-NMR data
(CDCl$_3$/TMS,
$\delta$ [ppm])

| No. | $R^5$ | $R^7$ | X | |
|---|---|---|---|---|
| Ia.01 | H | Cl | —CO— | |
| Ia.02 | F | Cl | —CO— | |
| Ia.03 | H | CN | —CO— | |
| Ia.04 | F | CN | —CO— | |
| Ia.05 | H | Cl | —O—CH$_2$—CO— | |
| Ia.06 | F | Cl | —O—CH$_2$—CO— | |
| Ia.07 | H | CN | —O—CH$_2$—CO— | |
| Ia.08 | F | CN | —O—CH$_2$—CO— | |
| Ia.09 | H | Cl | —O—CH(CH$_3$)—CO— | |
| Ia.10 | F | Cl | —O—CH(CH$_3$)—CO— | see Preparation Example |

TABLE 1-continued

Ia

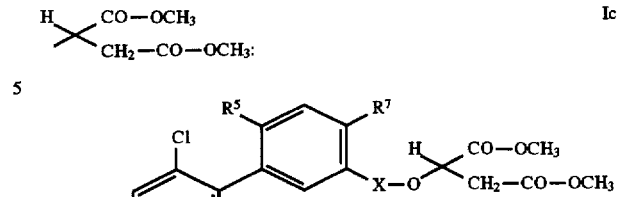

| No. | R⁵ | R⁷ | X | M.p. [°C.]; IR data ($\gamma[cm^{-1}]$); $^1$H-NMR data (CDCl$_3$/TMS, $\delta$ [ppm]) |
|---|---|---|---|---|
| Ia.11 | H | CN | $-O-CH(CH_3)-CO-$ | |
| Ia.12 | F | CN | $-O-CH(CH_3)-CO-$ | |
| Ia.13 | H | Cl | $-S-CH_2-CO-$ | |
| Ia.14 | F | Cl | $-S-CH_2-CO-$ | |
| Ia.15 | H | CN | $-S-CH_2-CO-$ | |
| Ia.16 | F | CN | $-S-CH_2-CO-$ | |
| Ia.17 | H | Cl | $-S-CH(CH_3)-CO-$ | |
| Ia.18 | F | Cl | $-S-CH(CH_3)-CO-$ | |
| Ia.19 | H | CN | $-S-CH(CH_3)-CO-$ | |
| Ia.20 | F | CN | $-S-CH(CH_3)-CO-$ | |
| Ia.21 | H | Cl | $-CH_2-CH(Cl)-CO-$ | |
| Ia.22 | F | Cl | $-CH_2-CH(Cl)-CO-$ | |
| Ia.23 | H | CN | $-CH_2-CH(Cl)-CO-$ | |
| Ia.24 | F | CN | $-CH_2-CH(Cl)-CO-$ | |
| Ia.25 | H | Cl | $-CH=C(Cl)-CO-$ | |
| Ia.26 | F | Cl | $-CH=C(Cl)-CO-$ | |
| Ia.27 | H | CN | $-CH=C(Cl)-CO-$ | |
| Ia.28 | F | CN | $-CH=C(Cl)-CO-$ | |
| Ia.29 | H | Cl | $-CH=C(CH_3)-CO-$ | |
| Ia.30 | F | Cl | $-CH=C(CH_3)-CO-$ | |
| Ia.31 | H | CN | $-CH=C(CH_3)-CO-$ | |
| Ia.32 | F | CN | $-CH=C(CH_3)-CO-$ | |

In addition, the following substituted 2-phenylpyridines of the formula I are particularly preferred:

the compounds Ib.01–Ib.32 which differ from the corresponding compounds Ia.01–Ia.32 only in that Z is tetrahydrofuran-3-yl:

Ib

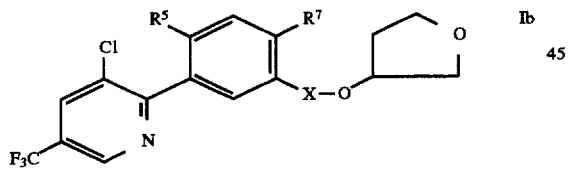

the compounds Ic.01–Ic.32 which differ only from the corresponding compounds Ia.01–Ia.32 in that Z is a Ic

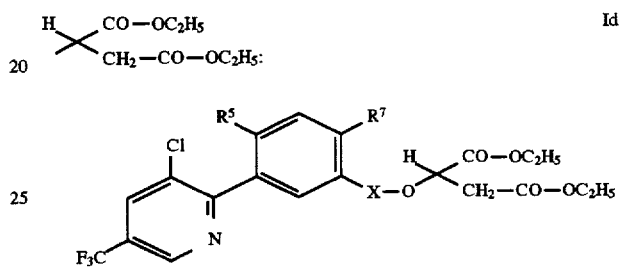

the compounds Id.01–Id.32 which differ only from the corresponding compounds Ia.01–Ia.32 in that Z is a group Id the compounds Ie.01–Ie.32 which differ only from the corresponding compounds Ia.01–Ia.32 in that Z is a group Ie

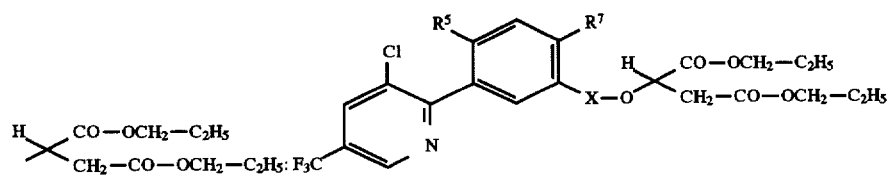

the compounds If.01–If.32 which differ only from the corresponding compounds Ia.01–Ia.32 in that Z is a group

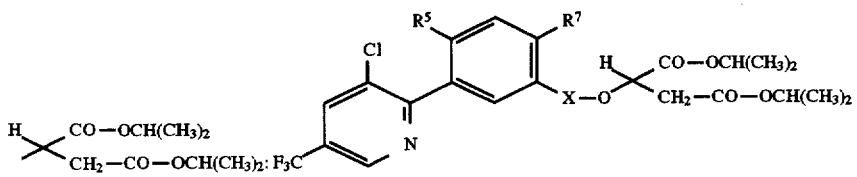

The substituted 2-phenylpyridines of the formula I are obtainable in various ways, for example by one of the following processes:

Process A:
Reaction of acid chlorides III with 3-hydroxytetrahydrofurans IV or alcohols V in the presence of a base (cf., for example, K. Furuta et al., Org. Synth. 72 (1993), 86 and H. Henecka in Houben-Weyl, Methoden der Organischen Chemie [Methods of Organic Chemistry], Vol. VIII, 4th Edition Stuttgart 1952, pages 463ff.):

G. H. Coleman et al., Org. Synth. Coll. Vol. III (1955), page 712;

H. Henecka in Houben-Weyl, Methoden der Organischen Chemie [Methods of Organic Chemistry], Vol. VIII, 4th Edition Stuttgart 1952, pages 463ff.

The carboxylic acids corresponding to the acid chlorides III are disclosed, for example, in DE-A 43 23 916 or obtainable in the manner described there.

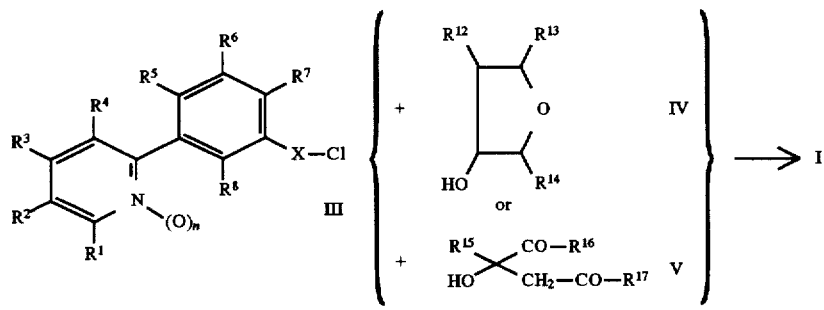

The reaction is customarily carried out in an inert solvent or diluent, in particular in a halogenated hydrocarbon such as dichloromethane, chloroform, 1,2-dichloroethane or carbon tetrachloride.

Suitable bases are, for example, alkali metal (hydrogen) carbonates such as sodium hydrogen carbonate and sodium carbonate, and further nitrogen bases such as pyridine, 4-dimethylaminopyridine and triethylamine.

The reaction temperature is normally from 0° to 100° C.

Customarily, the components are employed in approximately stoichiometric amounts, but an excess of one of the components, eg. with respect to an as complete as possible reaction of the other components, can be advantageous.

The acid chlorides of the formula III are novel. Expediently, they are prepared by chlorination of the corresponding free carboxylic acids or their alkali metal salts.

The chlorination can either be carried out without solvent in an excess of the halogenating agent or in an inert solvent or diluent, in particular in an aprotic solvent, eg. in diethyl ether, benzene or in carbon disulfide.

Suitable chlorinating agents are, for example, thionyl chloride, oxalyl chloride, phosphorus trichloride, phosphorus pentachloride, phosphorus oxychloride, phosgene, diphosgene or triphosgene.

Further details for carrying out chlorination reactions of this type are to be found in the following literature to which reference is made by way of example:

A. J. Meyers and M. E. Flanagan, Org. Synth. 71 (1992), 107;

H. J. Scheifele Jr. and D. F. DeTar, Org. Synth. Coll. Vol. IV (1963), page 34;

Process B:
Oxidation of substituted 2-phenylpyridines of the formula I in which n is zero in a manner known per se {cf., for example, A. Albini & S. Pietra, Heterocyclic N-Oxides, CRC Press Inc., Boca Raton, USA 1991; H. S. Mosher et al., Org. Synth. Coll. Vol. IV (1963), page 828; E. C. Taylor et al., Org. Synth. Coll. Vol. IV (1963), page 704; T. W. Bell et. al., Org. Synth. 69 (1990), page 226}:

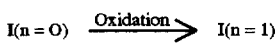

Among the oxidants customary for the oxidation of the pyridine ring, reference may be made by way of example to peracetic acid, trifluoroperacetic acid, perbenzoic acid, m-chloroperbenzoic acid, monopermaleic acid, magnesium monoperphthalate, sodium perborate, Oxone®(contains peroxydisulfate), pertungstic acid and hydrogen peroxide.

Suitable solvents are, for example, water, sulfuric acid, carboxylic acids such as acetic acid and trifluoroacetic acid, and halogenated hydrocarbons such as dichloromethane and chloroform.

The oxidation normally takes place at from 0° C. to the boiling point of the reaction mixture.

The oxidant is normally employed in at least equimolar amounts, based on the starting compound. In general, an excess of oxidant has proven particularly advantageous.

Process C:
Reaction of 3-pyridylphenols of the formula VII with tetrahydrofuryl esters VIII or esters IX in the presence of a base:

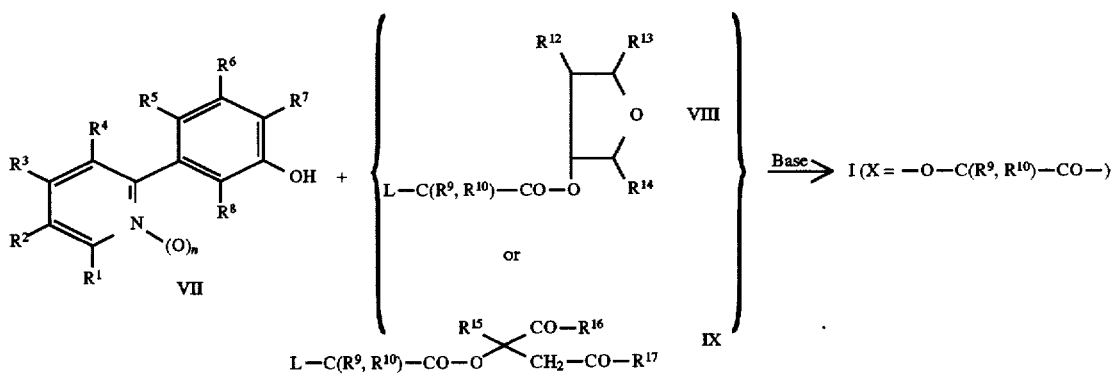

L is chlorine, bromine, iodine, methylsulfonyloxy, trifluoromethylsulfonyloxy, phenylsulfonyloxy or p-tolylsulfonyloxy.

The reaction is generally carried out in an inert solvent or diluent which is preferably aprotic, ie., for example, in N,N-dimethylformamide, dimethyl sulfoxide, acetone, N-methylpyrrolidone, acetonitrile or in an ether such as diethyl ether, tetrahydrofuran or 1,4-dioxane.

Bases which can be used are, for example, alkali metal carbonates and hydrogen carbonates such as sodium hydrogen carbonate, potassium hydrogen carbonate, sodium carbonate and potassium carbonate, alkali metal alkoxides such as sodium methoxide and potassium tert-butoxide, alkali metal hydroxides such as sodium hydroxide, and alkali metal hydrides such as sodium hydride.

Further details for carrying out alkylation reactions of this type are to be found, for example, in the following literature:

for the alkylation of phenols with α-carbonylsulfonates:

U. Burkard and F. Effenberger, Chem. Ber. 119 (1986), 1594;

J. Bierdermann et al., J. Med. Chem. 29 (1986), 1183;

R. B. Rogers et al., U.S. Pat. No. 4,725,683.

for the alkylation of phenols with α-haloesters:

R. Aneja et al., Tetrahedron 2 (1958), 203;

EP-A 380 043;

C. R. Edwards et al., J. Heterocycl. Chem. 24 (1987), 495;

C. P. Phadke et al., Synthesis 5 (1986), 413;

K. G. Watson, U.S. Pat. No. 4,837,355;

V. Elango et al., U.S. Pat. No. 4,908,476;

G. Schlegel et al., U.S. Pat. No. 4,978,774;

U. Burkard und F. Effenberger, Chem. Ber. 119 (1986), 1594;

H. Sugihara et al., Chem. And Pharm. Bull. 35 (1987), 1919;

S. Fujinawa et al., U.S. Pat. No. 4,625,053.

The tetrahydrofuryl esters VIII and esters IX are known or obtainable in a manner known per se {see, for example, EP-A 548 593, U.S. Pat. No. 4,086,076 and H. G. Zachau and W. Krau, Chem. Ber. 93 (1960), 1830}.

Process D:

Reaction of 3-pyridylthiophenols of the formula X with tetrahydrofuryl esters VIII or esters IX in the presence of a base:

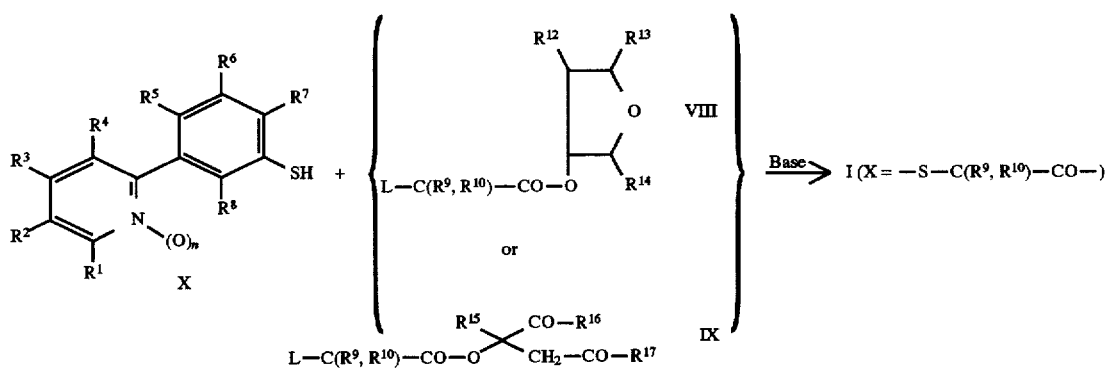

With respect to the definition of L and suitable solvents/diluents and bases, the details for process C apply.

Further details for carrying out alkylation reactions of this type are to be found, for example, in the following literature:

for alkylation of thiophenols with α-carbonylsulfonates:

U. Burkard und F. Effenberger, Chem. Ber. 119 (1986), 1594;

for alkylation of thiophenols with α-haloesters:

M. B. Floyd, U.S. Pat. No. 4,983,753;

E. Campaigne and A. R. McLaughlin, J. Heterocycl. Chem. 20 (1983), 623;

J. Durman et al., J. Chem. Soc. Perkin Trans. (1986), 1939;

M. Kawada et al., Chem. Pharm. Bull. 34 (1986), 1939;

H. Sugihara et al., Chem. And Pharm. Bull. 35 (1987), 1919.

If not stated otherwise, all processes described above are expediently performed at atmospheric pressure or under the autogenous pressure of the respective reaction mixture.

The reaction mixtures are generally worked up by methods known per se, for example by removing the solvent, partitioning the residue in a mixture of water and a suitable organic solvent and working up the organic phase to the product.

The substituted 2-phenylpyridines of the formula I can contain one or more centers of chirality and are then customarily obtained as enantiomer or diastereomer mixtures. If desired, the mixtures can be separated into the largely pure isomers by the methods which are customary for this purpose, eg. by means of crystallization or chromatography on an optically active adsorbate. Pure optically active isomers can also be prepared, for example, from corresponding optically active starting materials.

Substituted 2-phenylpyridines I containing CH-acidic substituents can be converted in a manner known per se into their salts, preferably into their alkali metal salts.

Salts of I whose metal ion is not an alkali metal ion can be prepared in a customary manner by double decomposition of the corresponding alkali metal salts, just as ammonium and phosphonium salts can be prepared by means of ammonia, phosphonium, sulfonium or sulfoxonium hydroxides.

These compounds I which carry a terminal amino group can further form acid addition salts.

The compounds I and their agriculturally utilizable salts are suitable as herbicides, both as isomer mixtures and in the form of the pure isomers. The herbicidal compositions containing I very effectively control plant growth on uncultivated areas, particularly at high application rates. They act against broad-leaved weeds and grass weeds in crops such as wheat, rice, maize, soybeans and cotton without noticeably damaging the crop plants. This effect occurs especially at low application rates.

Depending on the particular application method, the compounds I or herbicidal compositions containing them can additionally be employed in a further number of crop plants for eliminating undesired plants. Suitable crops, for example, are the following: *Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *sitvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum (N. rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

Moreover, the compounds I can also be used in crops which are tolerant toward the action of herbicides as a result of breeding, including genetic engineering methods.

In addition, the substituted 2-phenylpyridines I are also suitable for the desiccation and/or defoliation of plants.

As desiccants, they are in particular suitable for the desiccation of the above-ground parts of crop plants such as potato, oilseed rape, sunflower and soybean. Completely mechanized harvesting of these important crop plants is thus made possible.

Of economic interest is also the facilitation of harvesting, which is made possible by the temporally concentrated decrease or reduction in the power of adhesion to the tree in the case of citrus fruits, olives or in the case of other species and varieties of pomes, drupes and indehiscent fruit. The same mechanism, that is the promotion of the formation of separating tissue between fruit or leaf and stem part of the plants is also essential for a highly controllable defoliation of useful plants, in particular cotton.

Additionally, the shortening of the time interval in which the individual cotton plants become ripe leads to an enhanced fiber quality after harvesting.

The compounds I or the compositions containing them can be applied by spraying, atomizing, dusting, broadcasting or watering, for example in the form of directly sprayable aqueous solutions, powders, suspensions, also high-percentage aqueous, oily or other suspensions or dispersions, emulsions, oil dispersions, pastes, dusting compositions, broadcasting compositions or granules. The application forms depend entirely on the intended uses; in each case if possible, they should guarantee the finest dispersion of the active compounds according to the invention.

Suitable inert auxiliaries for the production of directly sprayable solutions, emulsions, pastes or oil dispersions are essentially: mineral oil fractions of medium to high boiling point such as kerosene and diesel oil, also coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone and water.

Aqueous application forms can be prepared from emulsion concentrates, dispersions, pastes, wettable powders or water-dispersible granules by addition of water. For the production of emulsions, pastes or oil dispersions, the substances as such or dissolved in an oil or solvent can be homogenized in water by means of wetting agents, adherents, dispersants or emulsifiers. However, concentrates consisting of active substance, wetting agents, adherents, dispersants or emulsifiers and possibly solvents or oil can also be prepared, which are suitable for dilution with water.

Suitable surface-active substances (adjuvants) are the alkali metal, alkaline earth metal or ammonium salts of aromatic sulfonic acids, eg. lignosulfonic acid, phenolsulfonic acid, naphthalenesulfonic acid and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols, as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenyl ether, ethoxylated isooctyl-, octyl- or nonylphenol, alkylphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be produced by mixing or joint grinding of the active substances with a solid carrier.

Granules, eg. coated, impregnated and homogeneous granules can be produced by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground plastics, fertilizers, such as ammonium sulfate, ammonium phosphate, ammonium nitrate, ureas and vegetable products such as cereal meal, tree bark, wood and nut-shell meal, cellulose powder or other solid carriers.

The concentrations of the active compounds I in the ready-to-apply preparations can be varied within wide ranges. The formulations generally contain from 0.001 to 98% by weight, preferably from 0.01 to 95% by weight, of active compound. The active compounds are in this case normally employed in a purity of from 90% to 100%, preferably from 95% to 100% (according to NMR spectrum).

The following formulation examples illustrate the preparation of such preparations:

I. 20 parts by weight of the compound No. Ia.10 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring the solution out and finely dispersing it in 100,000 parts by weight of water, an aqueous dispersion is obtained which contains 0.02% by weight of the active compound;

II. 20 parts by weight of the compound No. Ia.10 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound;

III. 20 parts by weight of the compound No. Ia.10 are dissolved in a mixture which consists of 25 parts by weight of cyclohexanone, 65 parts by weight of a mineral oil fraction of boiling point 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound;

IV. 20 parts by weight of the active compound No. Ia.10, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel are mixed well and ground in a hammer mill. By finely dispersing the mixture in 20,000 parts by weight of water, a spray liquor is obtained which contains 0.1% by weight of the active compound;

V. 3 parts by weight of the active compound No. Ia.10 are mixed with 97 parts by weight of finely divided kaolin. A dusting composition is obtained in this manner which contains 3% by weight of the active compound;

VI. 20 parts by weight of the active compound No. Ia.10 are intimately mixed with 2 parts by weight of the calcium salt of dodecylbenzenesulfonic acid, 8 parts by weight of fatty alcohol polyglycol ether, 2 parts by weight of the sodium salt of a phenol-urea-formaldehyde condensate and 68 parts by weight of a paraffinic mineral oil. A stable oily dispersion is obtained.

VII. 1 part by weight of the compound No. Ia.10 is dissolved in a mixture consisting of 70 parts by weight of cyclohexanone, 20 parts by weight of ethoxylated isooctylphenol and 10 parts by weight of ethoxylated castor oil. A stable emulsion concentrate is obtained.

VIII. 1 part by weight of the compound No. Ia.10 is dissolved in a mixture consisting of 80 parts by weight of cyclohexanone and 20 parts by weight of Emulphor EL[1]). A stable emulsion concentrate is obtained.

The application of the active compounds I or of the herbicidal compositions can be carried out pre-emergence or post-emergence. If the active compounds are less tolerable to certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The application rates of active compound I are, depending on the target to be controlled, time of year and stage of growth from 0.001 to 3.0, preferably from 0.01 to 1 kg/ha of active substance (a.s.).

For widening the spectrum of action and for achieving synergistic effects, the substituted 2-phenylpyridines I can be mixed with numerous representatives of other herbicidal or growth-regulating active compound groups and applied together. For example, suitable mixture components are 1,2,4-thiadiazoles, 1,3,4-thiadiazoles, amides, aminophosphoric acid and derivatives thereof, aminotriazoles, analides, aryloxy/heteroaryloxyalkanoic acids and derivatives thereof, benzoic acid and derivatives thereof, benzothiadiazinones, 2-(hetaroyl/aroyl)-1,3-cyclohexanediones, heteroaryl aryl ketones, benzylisoxazolidinones, meta-$CF_3$-phenyl derivatives, carbamates, quinolinecarboxylic acid and derivatives thereof, chloroacetanilides, cyclohexane-1,3-dione derivatives, diazines, dichloropropionic acid and derivatives thereof, dihydrobenzofurans, dihydrofuran-3-ones, dinitroanilines, dinitrophenols, diphenyl ethers, bipyridyl, halocarboxylic acids and derivatives thereof, ureas, 3-phenyluracils, imidazols, imidazolinones, N-phenyl-3,4,5, 6-tetrahydrophthalimides, oxadiazoles, oxiranes, phenols, aryloxy- and heteroaryloxyphenoxypropionic esters, phenylacetic acid and derivatives thereof, 2-phenylpropionic acid and derivatives thereof, pyrazoles, phenylpyrazoles, pyridazines, pyridinecarboxylic acid and derivatives thereof, pyrimidyl ethers, sulfonamides, sulfonylureas, triazines, triazinones, triazolinones, triazolecarboxamides and uracils.

It may additionally be of use to mix the compounds I, on their own or in combination with other herbicides, additionally with further plant protection compositions and to apply them together, for example with pesticides, compositions against phytopathogenic fungi and against bacteria. Additionally of interest is the miscibility with mineral salt solutions, which are employed for the elimination of nutritional and trace element deficiencies. Non-phytotoxic oils and oil concentrates can also be added.

Preparation Example

Compound No. Ia.10 in Table 1

The preparation was carried out according to the following reaction equation:

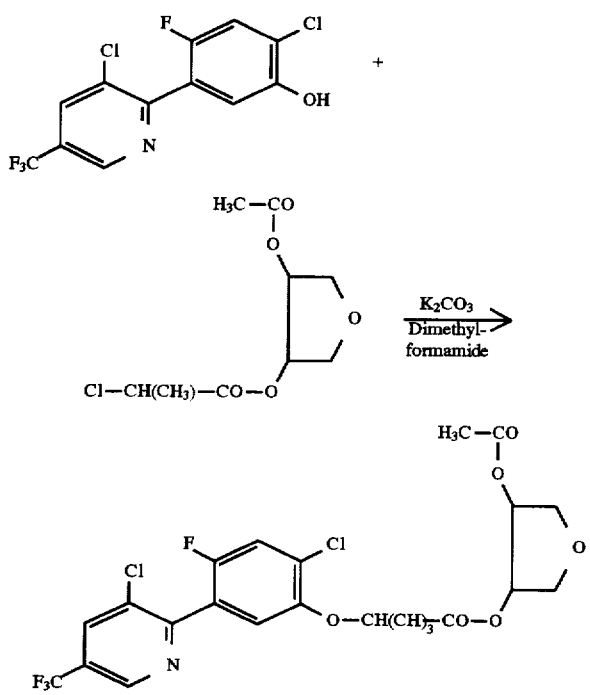

1.0 g of 3-chloro-2-(4-chloro-2-fluoro-5-hydroxyphenyl)-5-trifluoromethylpyridine, 1.1 g of (±)-(3R,4S)-4-acetoxy-3-(2-chloropropionyloxy)tetrahydrofuran and 0.85 g of potassium carbonate were stirred at 80° C. for three hours in 50 ml of anhydrous dimethylformamide. The cooled reaction mixture was then poured onto 200 ml of ice water, after which it was extracted three times with 100 ml of tert-butyl methyl ether each time. The combined organic phases were washed twice with 50 ml of water each time, dried over sodium sulfate and concentrated. Yield: 1.3 g (80%) of a colorless oil (diastereomer mixture).

$^1$H-NMR (270 MHz, in CDCl$_3$): δ[ppm]=1.67(d,3H; secondary diastereomer), 1.71(d,3H; main diastereomer), 1.97 (s,3H; secondary diastereomer), 2.00(s,3H; main diastereomer), 3.70–4.11(m,4H), 4.82(q,1H), 5.30(q,1H), 5.36–5.44(m, 1H), 7.06(d,1H), 7.29(d,1H), 8.05(s,1H), 8.84 (s,1H).

Precursor:

(±)-(3R,4S)-4-Acetoxy-3-(2-chloropropionyloxy)tetrahydrofuran 12.4 g of (±)-2-chloropropionyl chloride were added dropwise at 0°–5° C. to an ice-cooled mixture of 15.0 g of (±)-(3R,4S)-3-hydroxy-4-methylcarbonyloxytetrahydrofuran, 8.1 g of anhydrous pyridine and 200 ml of anhydrous dichloromethane. After addition was complete, the reaction mixture was stirred at 23° C. for a further 4 hours, after which it was poured onto 400 ml of water. The organic phase was then separated off, washed twice with 50 ml of water each time, dried over sodium sulfate and finally concentrated. The crude product was purified by distillation at a pressure of 10 mbar.

Yield: 15.7 g (68%) of a colorless oil.

$^1$H-NMR (270 MHz, in CDCl$_3$): δ[ppm]=1.73(d,3H), 2.09(s,3H), 3.80–3.92(m,2H), 4.07–4.16(m,2H), 4.45(q,1H), 5.33–5.44(m,2H).

Use examples (herbicidal activity)

It was possible to show the herbicidal action of the substituted 2-phenylpyridines I by greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered to promote germination and growth, and then covered with transparent plastic hoods until the plants had taken root. This covering causes uniform germination of the test plants if this has not been adversely affected by the active compounds.

For the purpose of post-emergence treatment, the test plants were first raised, depending on growth form, up to a growth height of from 3 to 15 cm, and only then treated with the active compounds suspended or emulsified in water. For this purpose, the test plants were either sown directly and cultivated in the same containers or they were first raised separately as seedlings and transplanted into the test containers a few days before treatment. The application rate for post-emergence treatment was 0.0078 or 0.0039 kg/ha of a.s. (active substance).

The plants were kept in a species-specific manner at 10°–25° C. or 20°–35° C. The test period extended over 2 to 4 weeks. During this time, the plants were tended and their reaction to the individual treatments was evaluated.

Assessment was carried out on a scale from 0 to 100. 100 in this case means no emergence of the plants or complete destruction at least of the above-ground parts and 0 means no damage or normal course of growth.

The plants used in the greenhouse tests consist of the following species:

| Botanical name | Common name |
|---|---|
| Abutilon theophrasti | velvet leaf |
| Amaranthus retroflexus | redroot pigweed |
| Ipomoea subspecies | morning-glory |
| Solanum nigrum | black nightshade |

At an application rate of 0.0078 or 0.0039 kg/ha of a.s. the compound No. Ia.10 showed a very good action against the abovementioned plants postemergence Use examples (desiccant/defoliant activity)

The test plants used were young, 4-leaved (without seed leaves) cotton plants, which were raised under greenhouse conditions (rel. atmospheric humidity 50 to 70%; day/night temperature 27°/20° C.).

The young cotton plants were subjected to foliar treatment until dripping wet with aqueous preparations of the active compounds (with addition of 0.15% by weight of the fatty alcohol alkoxylate Plurafac LF 700, based on the spray liquor). The amount of water applied was the equivalent of 1000 l/ha. After 13 days, the number of leaves shed and the degree of defoliation was determined in %.

In the case of the untreated control plants, no leaf fall occurred.

We claim:
1. A substituted 2-phenylpyridine of the general formula I

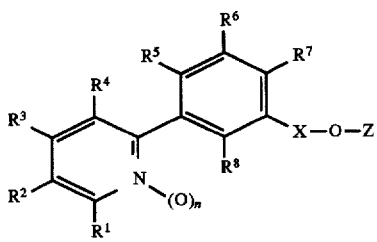

where the variables have the following meanings:

n is 0 or 1;

$R^1$, $R^3$ and $R^4$ independently of one another are hydrogen, halogen, $C_1$–$C_4$-alkyl, $C_1$–$C_4$-haloalkyl, hydroxyl, $C_1$–$C_4$-alkoxy, $C_1$–$C_4$-haloalkoxy, nitro, amino, $C_1$–$C_4$-alkylamino, di-($C_1$–$C_4$-alkyl)-amino, mercapto, $C_1$–$C_4$-alkylthio, $C_1$–$C_4$-haloalkylthio, cyano, carboxyl, ($C_1$–$C_4$-alkoxy)carbonyl, aminocarbonyl, $C_1$–$C_4$-alkylaminocarbonyl or di-($C_1$–$C_4$-alkyl) aminocarbonyl;

$R^2$ is hydrogen, halogen, $C_1$–$C_4$-alkyl, $C_1$–$C_4$-haloalkyl, cyano, nitro, amino, hydroxyl, $C_1$–$C_4$-alkoxy, $C_1$–$C_4$-haloalkoxy, mercapto, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^5$ is hydrogen, halogen or cyano;

$R^6$ and $R^8$ independently of one another are hydrogen or halogen;

$R^7$ is hydrogen, cyano, nitro, hydroxyl, trifluoromethylsulfonyloxy, halogen, $C_1$–$C_4$-alkyl, $C_1$–$C_4$-haloalkyl, $C_1$–$C_4$-alkoxy or $C_1$–$C_4$-haloalkoxy;

X is one of the following bridges: —CO—, —O—C($R^9$, $R^{10}$)—CO—, —S—C($R^9$,$R^{10}$)—CO—, —CH$^2$—CH($R^{11}$)—CO— or —CH=C($R^{11}$)—CO—, where $R^9$ and $R^{10}$ independently of one another are hydrogen or $C_1$–$C_4$-alkyl and $R^{11}$ is hydrogen, halogen or $C_1$–$C_4$-alkyl;

Z is a group

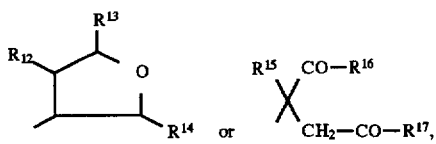

$R^{12}$ is hydrogen, hydroxyl, halogen, $C_1$–$C_4$-alkyl, $C_1$–$C_4$-alkoxy, ($C_1$–$C_4$-alkyl)carbonyloxy, ($C_1$–$C_4$-haloalkyl) carbonyloxy, ($C_3$–$C_6$-cycloalkyl)carbonyloxy, benzoyloxy, benzylcarbonyloxy, benzyloxy, ($C_1$–$C_4$-alkoxy)carbonyloxy, ($C_1$–$C_4$-alkylamino)carbonyloxy, di-($C_1$–$C_4$-alkyl)-aminocarbonyloxy or $C_1$–$C_3$-alkylsulfonyloxy;

$R^{13}$ and $R^{14}$ independently of one another are hydrogen, hydroxyl, $C_1$–$C_4$-alkyl, $C_1$–$C_4$-alkoxy or ($C_1$–$C_4$-alkyl) carbonyloxy;

$R^{15}$ is hydrogen or $C_1$–$C_4$-alkyl and $R^{16}$ and $R^{17}$ independently of one another are hydroxyl, $C_1$–$C_6$-alkoxy, $C_3$–$C_6$-alkenyloxy, $C_3$–$C_6$-alkynyloxy, $C_1$–$C_6$-alkoxy-$C_2$–$C_4$-alkoxy, $C_3$–$C_6$-cycloalkyloxy, amino, $C_1$–$C_4$-alkylamino, di-($C_1$–$C_4$-alkyl)-amino, N-pyrrolidinyl, N-piperidinyl, N-morpholinyl, $C_3$–$C_6$-cycloalkylamino, di-($C_3$–$C_6$-cycloalkyl)-amino, $C_3$–$C_6$-alkenylamino or $C_3$–$C_6$-alkynylamino or $R^{16}$ and $R^{17}$ together are a bridge —N($R^{18}$)—N($R^{19}$)— or —N($R^{20}$)—, where $R^{18}$ and $R^{19}$ are in each case hydrogen or $C_1$–$C_4$-alkyl and $R^{20}$ is hydrogen, $C_1$–$C_6$-alkyl, $C_3$–$C_6$-alkenyl, $C_3$–$C_6$-alkynyl, $C_1$–$C_6$-alkoxy or $C_3$–$C_6$-alkenyloxy, or the agriculturally utilizable salts of the compounds I.

2. A substituted 2-phenylpyridine of the formula I as claimed in claim 1, where n is zero, $R^1$, $R^3$ and $R^4$ independently of one another are hydrogen or halogen, $R^2$ is halogen or $C_1$–$C_4$-haloalkyl having one to five halogen atoms, $R^5$ is hydrogen or halogen, $R^6$ is hydrogen, $R^7$ is halogen or cyano, $R^8$ is hydrogen, $R^9$ and $R^{10}$ independently of one another are hydrogen or $C_1$–$C_4$-alkyl, $R^{11}$ is hydrogen or halogen, $R^{12}$, $R^{13}$ and $R^{14}$ independently of one another are hydrogen, $C_1$–$C_4$-alkyl, hydroxyl or ($C_1$–$C_4$-alkyl) carbonyloxy, $R^{15}$ is hydrogen, $R^{16}$ and $R^{17}$ independently of one another are $C_1$–$C_6$-alkoxy, $C_3$–$C_6$-alkenyloxy, amino, $C_1$–$C_4$-alkylamino, di-($C_1$–$C_4$-alkyl)amino or together are a bridge —NH—NH—, —N($C_1$–$C_4$-Alkyl)—N($C_1$–$C_4$-alkyl)- or —N($R^{20}$)— and $R^{20}$ is hydrogen or $C_1$–$C_6$-alkyl.

3. A herbicidal composition containing a herbicidally active amount of at least one substituted 2-phenylpyridine of the formula I or of an agriculturally utilizable salt of I, as claimed in claim 1, and at least one inert liquid and/or solid carrier and also, if desired, at least one surface-active substance.

4. A composition for the desiccation and/or defoliation of plants, containing an amount of at least one substituted 2-phenylpyridine of the formula I or of an agriculturally utilizable salt of I, as claimed in claim 1, which has desiccant and/or defoliant activity, and at least one inert liquid and/or solid carrier and also, if desired, at least one surface-active substance.

5. A process for preparing herbicidally active compositions, which comprises mixing a herbicidally active amount of at least one substituted 2-phenylpyridine of the formula I or of an agriculturally utilizable salt of I, as claimed in claim 1, and at least one inert liquid and/or solid carrier and also, if desired, at least one surface-active substance.

6. A process for preparing compositions having desiccant and/or defoliant activity, which comprises mixing an amount of at least one substituted 2-phenylpyridine of the formula I or of an agriculturally utilizable salt of I, as claimed in claim 1, having desiccant and/or defoliant activity, and at least one inert liquid and/or solid carrier and also, if desired, at least one surface-active substance.

7. A method of controlling undesired vegetation, which comprises allowing a herbicidally active amount of at least one substituted 2-phenylpyridine of the formula I or of an agriculturally utilizable salt of I, as claimed in claim 1, to act on plants, their habitat or on seed.

8. A method for the desiccation and/or defoliation of plants, which comprises allowing an amount of at least one substituted 2-phenylpyridine of the formula I or of an agriculturally utilizable salt of I, as claimed in claim 1, having dessicant and/or defoliant activity, to act on plants.

9. A method as claimed in claim 8, wherein cotton is treated.

10. A process for preparing substituted 2-phenylpyridines of the formula I as claimed in claim 1, where Z is the group

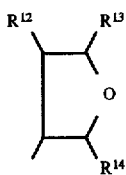

which comprises reacting an acid chloride of the formula III

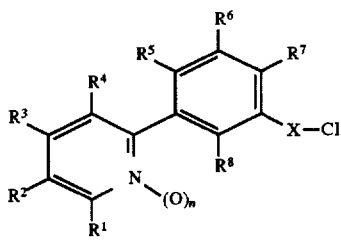

in a manner known per se in an inert solvent or diluent, in the presence of a base, with a 3-hydroxytetrahydrofuran of the formula IV

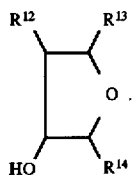

11. A process for preparing substituted 2-phenylpyridines of the formula I as claimed in claim 1, where Z is the group

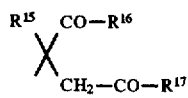

which comprises reacting an acid chloride of the formula III

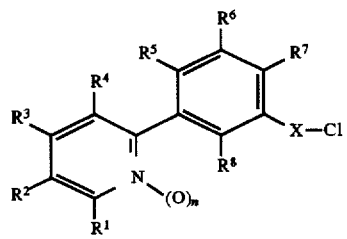

in a manner known per se in an inert solvent or diluent, in the presence of a base, with an alcohol of the formula V

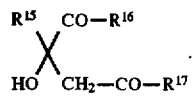

12. An acid chloride of the formula III

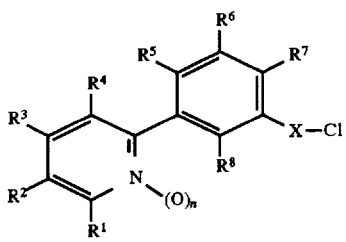

where the variables have the following meanings:

n is 0 or 1;

$R^1$, $R^3$ and $R^4$ independently of one another are hydrogen, halogen, $C_1$–$C_4$-alkyl, $C_1$–$C_4$-haloalkyl, hydroxyl, $C_1$–$C_4$-alkoxy, $C_1$–$C_4$-haloalkoxy, nitro, amino, $C_1$–$C_4$-alkylamino, di-($C_1$–$C_4$-alkyl)-amino, mercapto, $C_1$–$C_4$-alkylthio, $C_1$–$C_4$-haloalkylthio, cyano, carboxyl, ($C_1$–$C_4$-alkoxy)carbonyl, aminocarbonyl, $C_1$–$C_4$-alkylaminocarbonyl or di-($C_1$–$C_4$-alkyl) aminocarbonyl;

$R^2$ is hydrogen, halogen, $C_1$–$C_4$-alkyl, $C_1$–$C_4$-haloalkyl, cyano, nitro, amino, hydroxyl, $C_1$–$C_4$-alkoxy, $C_1$–$C_4$-haloalkoxy, mercapto, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^5$ is hydrogen, halogen or cyano;

$R^6$ and $R^8$ independently of one another are hydrogen or halogen;

$R^7$ is hydrogen, cyano, nitro, hydroxyl, trifluoromethylsulfonyloxy, halogen, $C_1$–$C_4$-alkyl, $C_1$–$C_4$-haloalkyl, $C_1$–$C_4$-alkoxy or $C_1$–$C_4$-haloalkoxy;

X is one of the following bridges: —CO—, —O—C($R^9$, $R^{10}$)—CO—, —S—C($R^9$, $R^{10}$)—CO—, —CH$_2$—CH($R^{11}$)—CO— or —CH=C($R^{11}$)—CO—, where $R^9$ and $R^{10}$ independently of one another are hydrogen or $C_1$–$C_4$-alkyl and $R^{11}$ is hydrogen, halogen or $C_1$–$C_4$-alkyl.

13. A process for preparing the acid chlorides of the formula III as claimed in claim 12, which comprises chlorinating the corresponding free carboxylic acids or their alkali metal salts in a manner known per se.

14. A process for preparing substituted 2-phenylpyridines of the formula I as claimed in claim 1, where n is 1, which comprises oxidizing the corresponding substituted 2-phenylpyridines, where n is zero, in a manner known per se in an inert solvent or diluent.

15. A process for preparing substituted 2-phenylpyridines of the formula I as claimed in claim 1, where X is a bridge —O—C($R^9$, $R^{10}$)—CO—, which comprises reacting a 3-pyridylphenol of the formula VI

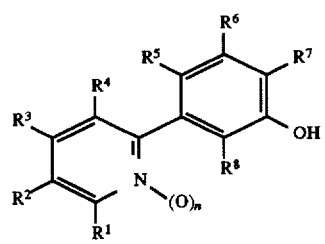

in a manner known per se in an inert solvent or diluent, in the presence of a base, with a tetrahydrofuryl ester of the formula VII

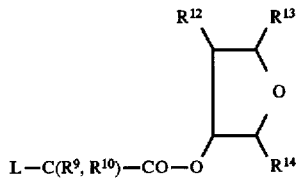

VII or an ester of the formula VIII

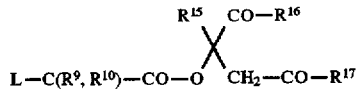

VIII where L in each case is chlorine, bromine, iodine, methylsulfonyloxy, trifluoromethylsulfonyloxy, phenylsulfonyloxy or p-toluenesulfonyloxy.

16. A process for preparing substituted 2-phenylpyridines of the formula I as claimed in claim 1, where X is a bridge —S—C($R^9$, $R^{10}$)—CO—, which comprises reacting a 3-pyridylthiophenol of the formula IX

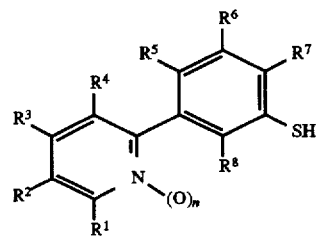

IX in a manner known per se in an inert solvent or diluent, in the presence of a base, with a tetrahydrofuryl ester of the formula VII

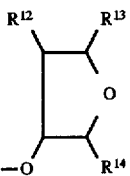

VII or an ester of the formula VIII

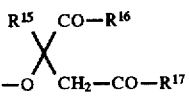

VIII where L in each case is chlorine, bromine, iodine, methylsulfonyloxy, trifluoromethylsulfonyloxy, phenylsulfonyloxy or p-tolylsulfonyloxy.

* * * * *

UNITED STATES PATENT AND TRADEMARK OFFICE
CERTIFICATE OF CORRECTION

PATENT NO.: 5,733,850

DATED: March 31, 1998

INVENTOR(S): SCHAEFER et al.

It is certified that error appears in the above-identified patent and that said Letters Patent is hereby corrected as shown below:

Column 21, claim 1, line 24, "aminocarbonyi" should be --aminocarbonyl--.

Column 21, claim 1, line 39, "$CH^2$" should be --$CH_2$--.

Column 21, claim 1, line 50, after the formulae, insert --where--.

Signed and Sealed this

Twenty-sixth Day of May, 1998

Attest:

BRUCE LEHMAN

Attesting Officer     *Commissioner of Patents and Trademarks*